US010441453B2

(12) United States Patent
Allen

(10) Patent No.: US 10,441,453 B2
(45) Date of Patent: Oct. 15, 2019

(54) ARM RESTRAINT FOR SURGERY TABLES

(71) Applicant: Robert Dan Allen, Newbury, OH (US)

(72) Inventor: Robert Dan Allen, Newbury, OH (US)

( * ) Notice: Subject to any disclaimer, the term of this patent is extended or adjusted under 35 U.S.C. 154(b) by 490 days.

(21) Appl. No.: 14/658,671

(22) Filed: Mar. 16, 2015

(65) Prior Publication Data
US 2015/0257920 A1 Sep. 17, 2015

Related U.S. Application Data

(60) Provisional application No. 61/952,960, filed on Mar. 14, 2014.

(51) Int. Cl.
*A61F 5/00* (2006.01)
*A61F 5/37* (2006.01)

(52) U.S. Cl.
CPC .................. *A61F 5/3761* (2013.01)

(58) Field of Classification Search
CPC .. A61F 5/0584; A61F 5/0585; A61F 5/05858; A61F 5/05866; A61F 5/37; A61F 5/3723; A61F 5/373; A61F 5/3761; A61F 5/3769; A61F 5/3776; A61F 5/3784; A61F 5/3792; A61G 7/065; A61G 7/075; A61G 7/1082; A61G 7/1092; A61G 7/1094; A61G 13/12; A61G 13/124; A61G 13/122; A61G 13/1235; A61G 13/1245
USPC ....... 128/878, 874, 875, 876, 877, 881, 882, 128/845, 86, 134, 133; 5/600, 613, 630, 5/621, 623, 646, 647, 628; 602/15; 378/209
See application file for complete search history.

(56) References Cited

U.S. PATENT DOCUMENTS

| 2,551,617 | A | * | 5/1951 | Maybert | A61M 5/52 128/877 |
| 3,931,654 | A | * | 1/1976 | Spann | A61F 5/3761 5/650 |
| 4,488,715 | A | * | 12/1984 | Comeau | A61G 13/12 5/647 |
| 4,662,366 | A | * | 5/1987 | Tari | A61F 5/3723 128/877 |
| 5,211,185 | A | * | 5/1993 | Garth | A61F 5/05883 128/876 |
| 5,216,772 | A | * | 6/1993 | Clute | A47D 13/08 5/630 |
| 5,228,457 | A | * | 7/1993 | Kawamura | A61B 46/10 128/846 |

(Continued)

OTHER PUBLICATIONS

"Aorn Guidelines for Tucking Arms", Perioperative Standards and Recommended Practice, 2009.

*Primary Examiner* — Keri J Nelson
*Assistant Examiner* — Adam Baker
(74) *Attorney, Agent, or Firm* — Pearne & Gordon LLP

(57) ABSTRACT

An arm restraint system is provided for restraining movement of an arm of a patient's body lying over a top surface of a table. The system includes a rigid support frame located at a lateral edge of said table and a padded restraint configured to at least partially receive the arm of said patient. The padded restraint is securely fixed to the rigid support frame, via a repositionable fastener, to inhibit movement of the patient's arm relative to the rigid support frame and thereby maintain the arm at a position laterally adjacent to the patient's body without the arm being restrained by tucking.

15 Claims, 6 Drawing Sheets

(56) References Cited

U.S. PATENT DOCUMENTS

| | | | | |
|---|---|---|---|---|
| 5,479,471 A | * | 12/1995 | Buckland | A61F 5/3761 |
| | | | | 128/845 |
| 5,957,874 A | * | 9/1999 | Klein | A61F 5/0195 |
| | | | | 128/882 |
| 6,898,810 B2 | * | 5/2005 | Steven | A61B 6/0442 |
| | | | | 5/601 |
| 8,539,621 B2 | | 9/2013 | West | |
| 8,539,622 B2 | | 9/2013 | West | |
| 8,539,623 B2 | | 9/2013 | West | |
| 8,601,623 B1 | | 12/2013 | West | |
| 8,646,457 B2 | | 2/2014 | Maynard et al. | |
| 2011/0009789 A1 | * | 1/2011 | Barns | A61F 5/055 |
| | | | | 602/17 |
| 2011/0100374 A1 | * | 5/2011 | Silfverskiold | A61F 5/05 |
| | | | | 128/845 |

\* cited by examiner

ARM RESTRAINT FOR SURGERY TABLES

CROSS-REFERENCE TO RELATED APPLICATIONS

This application claims the benefit of U.S. Provisional Application No. 61/952,960, filed Mar. 14, 2014, the entire disclosure of which is hereby incorporated herein by reference.

FIELD OF THE INVENTION

The present invention relates generally to patient restraints for surgery tables, and more particularly, to a patient arm restraint system for an operating room table.

BACKGROUND OF THE INVENTION

A number of operating room table accessory devices have been developed in an attempt to safely restrain patients from moving on the surgical table while laying in the supine position. The supine position may be maintained when the table is horizontal, tipped laterally or tipped into a head up angulation or into a down angulation a position known in the industry as the Trendelenburg position where the angle of head down tilt typically ranges from 20° to 50° with respect to a ground surface.

It is well-known in the medical industry that, for performing modern surgical procedures requiring supine the upper extremities are to be restrained at the side of the patient. Traditional wisdom has dictated that the arms be restrained by wrapping a linen or a disposable draw sheet around the arm which is then tucked beneath the patient or the mattress. Historically, when positioning patients for surgical procedures requiring that the patient's arms are held against the patient's body, the surgical team has used woven or non-woven sheets to bundle the arm against the side of the body. One risk of operating room acquired patient nerve injury occurs when the arm is bundled and held against the body with excessive compression. Another known risk factor is that surgeon(s) or assistant(s) often inadvertently lean against the patient's arm when attempting to remain within an ergonomic arms-length of the operative site or while attempting to stabilize their posture if they become fatigued. Other, more serious, patient risks include instances when the patient monitoring lines may become disengaged or an intravenous line may become dislodged, kinked or occluded leading to a disruption in the flow of IV fluids. The resultant emergent situation requires that the anesthesia caregiver gain immediate access to the affected site. This normally requires time consuming "un-bundling" of the arm. After the refastening or repositioning or clearing the occlusion of the lines an even more difficult and time consuming re-bundling, of the arm is necessary.

Gaining rapid access to the upper extremity is important when the patient monitoring lines may become disengaged or an intravenous line may become dislodged, kinked or occluded leading to a disruption in the flow of IV fluids. Dealing with those issues often occurs when the patient is in the extreme head down tilted posture (Trendelenburg position). The risks of neuropathy increase when, after the emergency has been dealt with, the arm is not re-tucked properly. Problems with re-tucking occurs often when the team has reduced access to the draw sheet when the patient is covered with a surgical drape, in a darkened room and postured in 30° to 40° of Trendelenburg (head down tilt). The combination of the tilt of the table, gravity and weight of the appendage against a loosened restraint is known to be responsible for arms slipping out of the tucking restraint, and falling freely to the side which is known to create very serious injuries. This reportable event is considered to be extremely serious and places the patient at risk for painful and debilitating nerve and muscle injury.

Moreover, it is not uncommon in the performance of Minimally Invasive Surgery of organs of the pelvis as well for Robotic assisted surgery of organs of the pelvis that the patient's arms are restrained against the patient's body when the operating room table is tilted so that the patient is in an extreme head down tilted position (The Trendelenburg Position). Added to the normal degree of difficulty in "re-bundling" the patient arm is the fact that during the surgical procedure the patient is hidden under a sterile protective drape, in a darkened room, postured in an extreme head down position. While the "un-bundling" allows for repair or repositioning of the lines the "re-bundling" is difficult to properly accomplish. This is especially apparent when it must be done in a dark environment with the patient in an extreme head down posture while under the sterile protective drape. The "re-bundling" is often done so quickly and inadequately that it is commonly known that it is not an uncommon event that the weight of the arm combined with the effect of gravity will pull the arm free from the improperly "re-bundled" sheet.

It has been reported in the medical literature that compression related to tucking arms can be causal to neuropathy (nerve injuries). The Association of Operating Room Nurses (AORN) is the recognized governing body for developing the guidelines used by operating room nurses to position patients. In 2010, AORN issued specific guidelines on patient positioning recommending against the tucking of arms. Patient risks associated with tucking include: wrinkles in the draw sheet, arms sagging below the top level of the mattress, interference with physiologic monitoring and the inability to resuscitate during an emergency due to unrecognized IV infiltration in the tucked arm. There is also an increased risk for the patient to develop compartment syndrome in the upper extremity. Other risk factors for injury include surgeon(s) or assistant(s) inadvertently leaning directly against the patient's arm when attempting to remain within an ergonomic arms-length of the operative site or while attempting to stabilize their posture if they become fatigued.

A number of operating room table accessory devices have been developed in an attempt to restrain patient's arms at their sides during certain surgical interventions. One common concept includes the utilization of what is known in the industry as a toboggan restraint, which is a protective plastic containment shell fabricated with an integral horizontal component that slides under the surface of the operating room pad and is commonly kept in position by gravity and the patient's body weight bearing down on the device. The containment shell is lateral to the patient's arm which is often wrapped in a protective material such as egg crate foam or a gel material. The toboggan is then used to push the arm against the body using un-measurable compressive forces that are known in the medical literature to have caused nerve injury by placing strain on joints, nerves and vessels of the upper extremity involved. This is particularly critical if a patient has limited mobility or if the joints are affected by degenerative disease or damaged from injuries. The issue of "tucking and re-tucking" the arm after an emergent circumstance is only slightly less complicated than when tucking the arms with woven or non-woven materials such as linen.

Contemporary ergonomic issues include the common complaint of surgeons and surgical assistants that leaning against the "toboggan" arm restraint, in an attempt to remain within an ergonomic arms-length of the operative site or while attempting to stabilize their posture, is very uncomfortable. Most recently it has been discovered that when attempting to use the toboggan during robotic assisted laparoscopic procedures, the physical height of the toboggan is known to cause physical interference (often referred to as clashing) with the robotic arm which is often in close proximity to the side of the patient's body. This interference is known to restrict the range of motion required by the robotic arm and keeps it from performing optimally.

Another conventional device that emulates the setup and utility of woven or nonwoven sheets that are used for tucking arms utilizes foam sheets with self-adhering hook and loop fasteners that allow the foam fabric to wrap around the arm to hold it in place (one example shown in the photographs labelled as "prior art"). The device functions in much the same manner as tucking arms and offers little lateral support or protection for the arm. The absence of lateral support also increases the inherent risks that occur when the surgeon(s) or assistant(s) lean directly against the extremity. The device does not provide horizontal support for arms of large patients that extend beyond the outer edge of the operating room table mattress. This results in the arm sagging and exacerbates the risk of the arm coming into contact with the hard edged surface of the accessory rail of the table. This is known to cause irreparable nerve injury.

This instant invention results from an attempt to provide an innovative device that eliminates or minimizes intraprocedural patient injury, meets or exceeds the clinical guidelines in the medical literature described herein regarding needs for safety, and provides fast and easy anesthesia access and exposure to lines, IV's and ports.

It is to be understood that both the foregoing general description and the following detailed description present example and explanatory embodiments of the invention, and are intended to provide an overview or framework for understanding the nature and character of the invention as it is claimed. The accompanying drawings are included to provide a further understanding of the invention and are incorporated into and constitute a part of this specification. The drawings, photographs, and attachments illustrate various example embodiments of the invention, and together with the description, serve to explain the principles and operations of the invention.

BRIEF SUMMARY OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect of the present invention, an arm restraint system for restraining movement of an arm of a patient's body lying over a top surface of a table is provided. A rigid support frame is located at a lateral edge of said table adjacent to the arm of said patient's body and comprises a horizontal surface at least partially disposed underneath a mattress lying over a top surface of said table, and a vertical surface extending upwards from the horizontal surface and comprising a first repositionable fastener thereon. A padded restraint is configured to at least partially receive the arm of said patient and includes a deformable material. The padded restraint comprises a central body and a pair of tabs on the central body are movable relative to the central body. The tabs further comprise a second repositionable fastener that is compatible with the first repositionable fastener. The padded restraint is securely fixed to the vertical surface of the rigid support frame, via the second repositionable fastener of the tabs, to inhibit movement of the patient's arm relative to the rigid support frame and thereby maintain the arm at a position laterally adjacent to the patient's body without the arm being tucked underneath the patient.

In accordance with another aspect of the present invention, a padded restraint is provided for restraining movement of an arm of a patient's body lying over a top surface of a table. The padded restraint comprises a central body, a first pair of projections extending outwards from the central body and comprising a first cutout portion therebetween, and a second pair of projections extending outwards from the central body in a direction opposite the first pair of projections and comprising a second cutout portion therebetween. A pair of discrete flexible tabs is integral with the central body that are each connected to the central body via a living hinge and independently movable relative to the central body via the living hinge. The tabs further comprise a repositionable fastener on an exterior surface thereof. All of the central body, first pair of projections, second pair of projections, and pair of tabs comprise a monolithic body made of a deformable material.

It is to be understood that both the foregoing general description and the following detailed description present example and explanatory embodiments of the invention, and are intended to provide an overview or framework for understanding the nature and character of the invention as it is claimed. The accompanying drawings are included to provide a further understanding of the invention and are incorporated into and constitute a part of this specification. The drawings illustrate various example embodiments of the invention, and together with the description, serve to explain the principles and operations of the invention.

BRIEF DESCRIPTION OF THE DRAWINGS

The foregoing and other aspects of the present invention will become apparent to those skilled in the art to which the present invention relates upon reading the following description with reference to the accompanying drawings, in which.

DESCRIPTION OF EXAMPLE EMBODIMENTS

Figure 1:
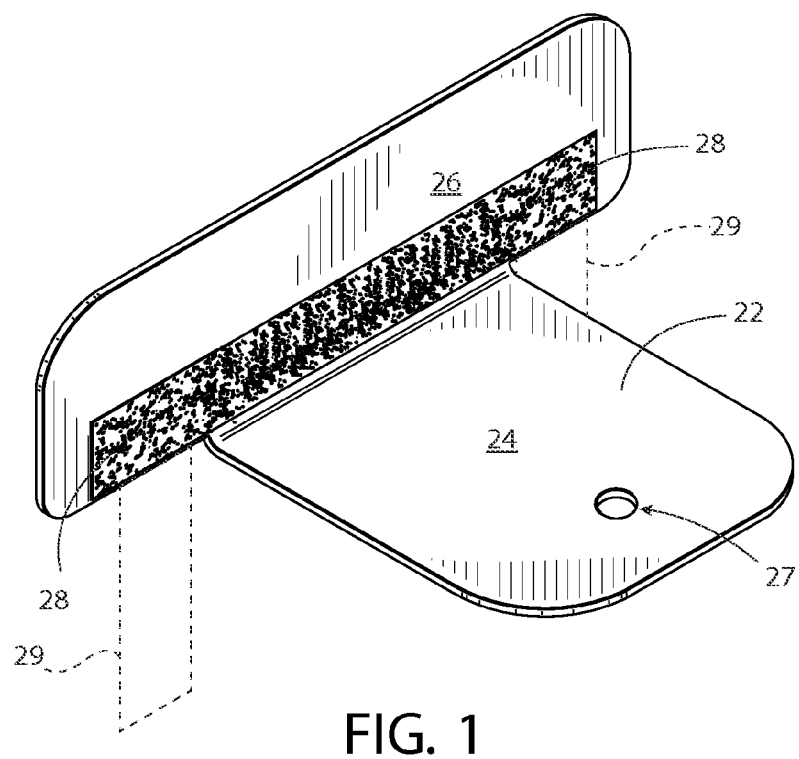
FIG. 1 illustrates a perspective view of an example rigid support frame.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

The present application relates generally to patient restraints for surgery tables, and more particularly, to a patient arm restrain device for an operating room table that is used to support, restrain, posture and/or expose the entirety of, or any portion of, one or both of a patient's arms before, during or after the completion of any surgical procedure or intervention. The primary role of the device is to provide a safe environment for the patient's arm during any surgical procedure requiring that the arm remain at the side of the patient during the surgical intervention.

The various objectives of the invention are to provide an improved restraint device for positioning patient arms at their sides. The invention results from an attempt to provide an innovative device that is capable of being utilized as: (1) a solution to the nursing guidelines against tucking arms as described herein; (2) to increase anesthesia care givers immediate access to faulty monitoring cables and non-functioning IV lines without having to untuck or "re-bundle" the extremity; (3) to provide a safe comfortable surface for surgeon(s) and assistant(s) to lean against while maintaining patient safety from compression risk; and (4) to provide an efficient support frame the design of which eliminates the potential for intraprocedural clashing of the robotic arm. These and other objectives are achieved by combining a support frame upon which may be attached infinitely adjustable padded or unpadded arm restraints, support or stabilizers according to the invention.

The arm restraint system 20 includes at least two major elements. The first element, shown in FIG. 1, is a rigid support frame 22 sometimes referred to as a sled. The rigid support frame 22 comprises a substantially horizontal surface 24 and a substantially vertical surface 26. In one example, the horizontal and vertical surfaces 24, 26 may be arranged substantially perpendicular to each other (i.e., 90 degrees+/−10 degrees), or could be arranged at another relative angle. In one embodiment, the rigid support frame 22 may be "hard attached" to the surgical table T accessory rail, such as via depending legs or the like, and in another embodiment, the rigid support frame 22 may be secured by sliding the horizontal surface 24 beneath the table mattress M and held by friction imparted by the patient's body mass. Physical or visual guides may be provided on the rigid support frame 22 that allow highly specific, precise and repeatable placement of primary or secondary padded arm restraints are located on the support frames. Each rigid support frame 22 additionally incorporates an aggressive releasable fastening system 28 across all or a portion of the vertical surface 26 that is compatible with that on the padded restraint. Preferably, the fastening system 28 extends across a lower aspect of the vertical surface 26, although it could extend across a central aspect or upper aspect, or even across a substantial portion or even all of the vertical surface 26. Lastly, either or both of the horizontal and vertical surfaces 24, 26 may include structure to enable the rigid support frame 22 to be stored in a hanging manner, such as a hole 27, hook, or the like that can enable hanging storage on a wall, cart, table, cabinet, or the like.

Figure 2:
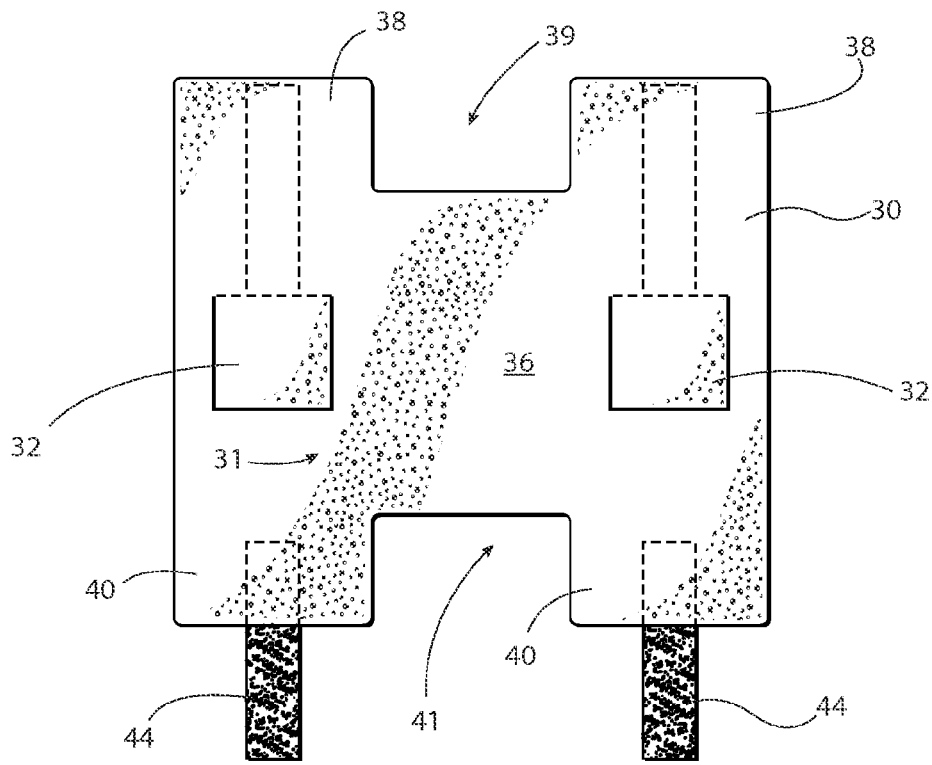
FIG. 2 illustrates a top view of an example padded restraint.
Figure 3:
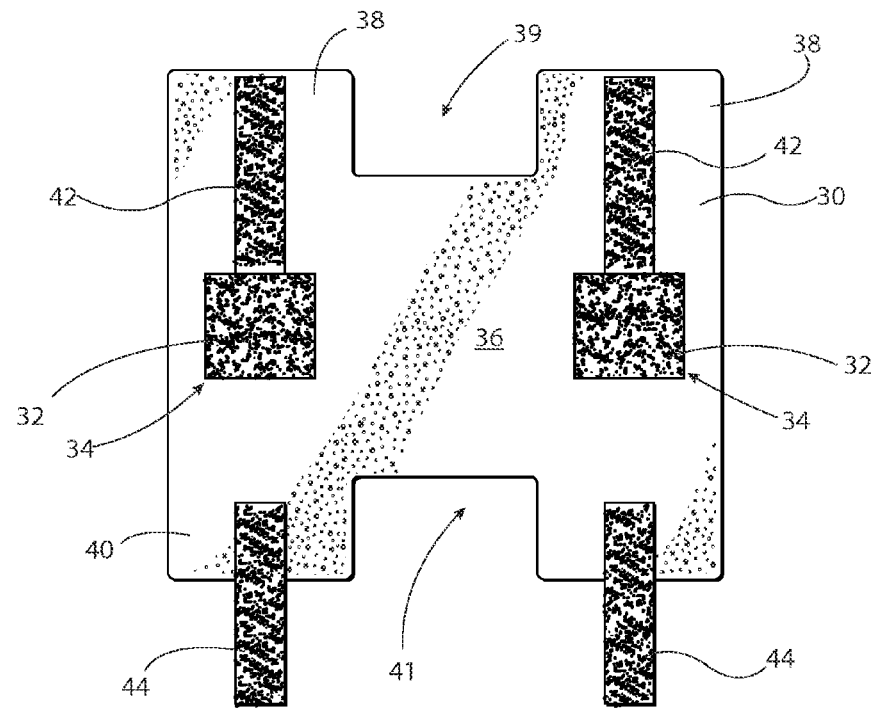
FIG. 3 is a bottom view of the example padded restraint.

The second element of the arm restraint system 20 is a specially shaped, infinitely adjustable padded restraint 30, shown in FIGS. 2-3, that wraps and is fastened around a portion of the patient's arm. The padded restraint 30 features integral tabs 32 that utilize aggressive releasable secured fasteners 34 to secure it to the rigid support frame 22. When combined, the rigid support frame 22 and the padded restraint 30 provide a safe and secure environment for restraining a patient's arms at their side to provide upper extremity restraint in lateral, horizontal and vertical planes. As will be clear, it is contemplated that one combined rigid support frame 22 and the padded restraint 30 is used to separately restrain each arm (i.e., one for each arm).

The first element, the rigid support frame 22 or sled, is a device utilized for the attachment of patient positioning devices capable of safely restraining the horizontal and lateral movement of the arms positioned at the sides of patients undergoing surgical interventions while laying upon the top surface of any operating room table. In some embodiments multiple frames can be so mounted so as to support a single, particularly large or long arm, or even to simultaneously support multiple arms.

The rigid support frame 22 is fabricated from one or more pieces of rigid materials of such strength and dimension as to be capable of holding the proportional weight of the upper appendage of a patient with a high body mass index. The sled is preferably made of durable, rigid materials that are suitable for use in an operating room and surgical setting, such as various metals (e.g., stainless steel, aluminum, etc.) and plastics. Such materials may or may not be radiolucent.

In some embodiments the rigid support frame 22 can restrain or control the movement of a patient's arm by being secured to the surgical table T by gravity and the patient's weight by sliding the horizontal surface 24 of said frame 22 transversally under the operating room mattress M beneath the patient's torso. The rigid support frame 22 can have an acute bend (i.e., greater than 45° and preferably in the range of about 80-110°) that creates a relatively longer surface on the horizontal plane and a relatively shorter surface on the vertical plane. Preferably, the horizontal surface 24 is relatively longer than the vertical surface 26, but they can be the same or the vertical surface could even be longer. Sliding the horizontal surface of said rigid frame transversally under the operating room mattress M beneath the patient's torso will utilize friction, gravity and patient weight to secure said rigid frame during utilization. In such an embodiment, the horizontal surface 24 of the support frame shall be of such a length as to avoid coming into contact with the hook and loop fastener that is typically utilized to fix the patient mattress M to the operating room table. The rigid support frame 22 may be moved underneath the mattress M in a horizontal direction toward the foot or the head of the surgical table T as may be required to locate the arm restraint system 20 in the most advantageous position. The rigid support frame 22 may also be fabricated with one or more sections of material removed from the horizontal surface 24 in order to facilitate utilization of said rigid support frame 22 with operating tables with a perineal cutout or other projecting structures that may otherwise interfere with the level installation of the rigid support frame device.

One embodiment of said rigid support frame 22 may be mounted upon the surgical table T rail utilizing accessory clamps that permit said frame to be fixed to an accessory mounting rail R; such rail R being conventionally attached along the side of the operating room. In this configuration, the rigid support frame 22 or sled can include one or more fixed or adjustable width vertical legs 29, blades or posts being securable on the accessory rails on the side of the operating table using clamps. It is contemplated that at least one leg can be provided and used to secure the rigid support frame 22 upon the operating room table, and optionally two or more legs are used. In one example, a single leg could be centrally located with respect to the vertical surface 26, or even offset from the center, and is shaped and dimensioned to be inserted to be inserted into accessory clamps that are customarily associated with fixing accessories attached to an accessory mounting rail which is coupled to or integral with to operating room tables. In another example, a pair of legs 29 could be used on either side of the vertical surface that are also shaped and dimensioned to be inserted to be inserted into accessory clamps on an accessory mounting rail of an operating room table. The pair of legs 29 can be secured to the support frame 22 with a fixed width, or at least one leg can be laterally slidable (preferably two or more legs are slidable) on the support frame 22 to be width-adjustable to be more useful with different tables having different widths and configurations. One example pair of legs 29 is shown schematically in FIG. 1. It is contemplated that the pair of legs 29 could be coupled to or integral with either of the horizontal and vertical surfaces 24, 26. In one example, the pair of legs 29 could be integral with and an extension of the vertical surface 26, or alternatively could be part of the horizontal surface 24. Still, in other examples, the any or all of the legs 29 could be removable and/or adjustable relative to the horizontal and vertical surfaces 24, 26 (such as where at least one width adjustable leg is desired).

In another embodiment, the rigid support frame 22 can be height adjustable in order to avoid clashing with robotic arms when the rigid frame is being employed during robotic assisted surgical interventions. For example, the vertical surface 26 could be height adjustable relative to the horizontal surface 24, such as on a sliding pin clamp or the like, or one or more of the legs 29 (if present) could offer height adjustability. If one or more legs 29 are used with accessory clamps C on the accessory mounting rail R, height adjustability could be provided by a selective insertion depth of the legs into the accessory clamps. In yet another embodiment, the rigid support frame 22 can be of such a fixed height above the operating room table mattress M that will avoid clashing with robotic arms when said rigid frame is being employed during robotic assisted surgical interventions.

The vertical surface 26 has attached a quantity of an aggressive releasable, repositionable fastener 28 that extends across all or a portion of a suitable support surface. The repositionable fastener 28 allows adjustable, patient specific, placement of one or more padded restraints 30, and/or other supports or stabilizers, upon the rigid support frame 22. Preferably, the repositionable fastener 28 extends across a substantial or complete width of the vertical surface 26, as shown in FIG. 1, to allow substantially infinite adjustment of the padded restraints 30 and/or other supports or stabilizers upon the support surface. Any or all off the padded restraints 30, supports or stabilizers may also have a corresponding compatible, aggressive, releasable and repositionable fastener system (described below) for coupling to the rigid support frame 22. The repositionable fastener 28 can be disposed partially or completely over the vertical surface 26 of the support frame 22 as one single continuous unit (see example of FIG. 1), or two or more separate units (see example of FIG. 6). If separate units are used, the repositionable fastener 28 can have the same or different strengths or other properties. In one example, the repositionable fastener comprises a hook-and-loop type fastener. In other examples, the repositionable fastener 28 includes snaps, hooks, clasps, clips, elastic members, tape, removable or non-permanent adhesives, etc. or combinations thereof.

The repositionable fastener 28 can be secured variously to the vertical surface 26, such by a non-removable adhesive or other snaps, hooks, clasps, clips, elastic members, tape, etc. Although the vertical surface 26 is described as having the repositionable fastener 28 thereon, it is contemplated that the horizontal surface 24 could feature a repositionable fastener 28 for use with the padded restraint 30.

The second element of the arm restraint system 20 is a specially shaped, infinitely adjustable padded restraint 30 (see FIGS. 2-3) that wraps and is fastened around a portion of the patient's arm. The padded restraint 30 or pad provides a soft flexible patient arm restraint device that safely restrains a patient's arms at their side during a surgical intervention, and is compatible with all embodiments of the rigid support frames 22 discussed herein. The padded restraint 30 may be fabricated from single or multi-use flexible padding material of such thickness and density that may provide a safe environment for the patient's upper extremity. The flexible padding material is fabricated in a shape or configuration that, when wrapped around the patient's arm, exposes certain portions of the upper extremity located between the axilla (i.e., armpit) and the tips of the patient's fingers. These exposed portions can be useful for the anesthesia team to provide easy and immediate access to IV lines (intravenous) and monitoring lines.

The padded restraint 30 is preferably formed as a monolithic body utilizing a single material, although it can be formed of multiple components and/or multiple materials. The padded restraint 30 is intended only to stabilize the patient's arms against lateral and/or torsional movement, and the combination of materials used should provide stability for patients ranging from 45 lbs to greater than 450 lbs, and preferably greater than 750 lbs. Additionally, the material can be a natural or synthetic material in such a size or density that will maintain its shape and function and provide and maintain sufficient resistance to the patient's weight and gravity. The padded restraint 30 includes a deformable material, such as foam, rubber, plastic, fabric or the like, and more preferably the material is a resiliently deformable material. In one example, the padded restraint is made of polyether-type polyurethane foam and has a density of at least 1 lbs per cubic foot, and more preferably at least 1.8 lbs per cubic foot. Additionally, the foam material preferably has an indentation load deflection (ILD) rating of at least 30 lbs, more preferably at least 40 lbs. An ILD rating is a hardness measurement of foam that is typically measured in the number of pounds of pressure required to indent the foam by 25% using a 50 square inch indentation (sometimes referred to as the 25% ILD rating). It is understood that the example load ratings described above are only examples, and other values are contemplated. The use of a deformable material ensures no undue compression of the arm, which significantly reduces the risk of posturing related injury including pressure points, stretched nerves and constrictions. Additionally, the padded restraint allows easy manipulation of the position of the limb, making it possible to assure desired compression loading and orientation of the extremity.

As mentioned above, the padded restraint 30 can be a monolithic body, or can include two or more components. In one example, the padded restraint can be manufactured from a single piece of foam or other unitary material. In another example, the padded restraint can be co-manufactured (e.g., such as using fasteners, adhesives, co-molding, co-extrusion, etc.) using two or more materials. Moreover, the padded restraint can be disposable, limited use or reusable. In a reusable configuration, the padded restraint can include an outer covering 31 (shown schematically in FIG. 2) that is either replaceable (e.g., a washable or single-use covering) or the outer covering can be non-replaceable but suitable to be cleaned and sanitized per medical standards. Preferably, the outer covering 31 substantially completely covers the entire padded restraint 30 on all sides. For example, the padded restraint could have a plastic, gel or other medically-suitable material coated, laminated, etc. on its exterior. Preferably, the outer covering 31 is deformable to move together with the padded restraint.

In each embodiment, patient restraints, supports and stabilizers may be attached to and project from said frame 22 being attached to the vertical surface 26 of said frame 22 using corresponding aggressive, releasable fasteners 34 compatible with that utilized on the support frame or sled. The releasable fasteners 34 permit infinite adjustment and relocation of the padded restraint 30, and/or other supports or stabilizers, on the rigid support frame 22 that are being utilized to support or restrain the patient's arm at the side of the body. In one example, the repositionable fasteners 34 comprise a hook-and-loop type fastener. In other examples, the repositionable fastener 34 includes snaps, hooks, clasps, clips, elastic members, tape, removable or non-permanent adhesives, etc. or combinations thereof. In any event, the fasteners 34 should be compatible with and correspond to the fasteners 28 of the rigid support frame 22.

The padded restraint 30 is shaped to conform to and encompass the patient extremity to be supported. In one example, the padded restraint 30 as an arm support may be shaped in a form somewhat resembling the letter "H." That is, as shown in FIGS. 2-3, the padded restraint 30 can have a central body 36 with a first pair of projections 38 bounding a first cutout 39, and an opposite second pair of projections 40 bounding a second cutout 41. The first and second cutouts at least partially line up with each other, and preferably substantially line up with each other (possibly being a mirror image of each other) across a centerline of the central body 36. The first and second pair of projections 38, 40, together with the first and second cutouts 39, 41, can provide the padded restraint 30 with a generally "H"-shaped geometry. The inside of the padded restraint is intended for patient contact and is smooth. The deformable material further enhances the even re-distribution of pressure over the entire supported surface. In one example, the padded restraint is approximately 18.5" wide×20" tall×0.625" thick, although other shapes and sizes are contemplated.

The padded restrain further includes one or more integrated tabs 32 within the flexible padding material. The tabs 32 are located generally on the central body 36, and each tab is preferably in line with one of the first pair 38 and the second pair 40 of projections. Preferably, each one of the first pair 38 and the second pair 40 of projections are arranged in a straight line and may comprise a mirror image of each other along a center line of the padded restraint 30. Additionally, each tab 32 is preferably centrally located generally between one of the first pair 38 and the second pair 40 of projections. Preferably, the tabs 32 are monolithic with the padded restraint, and comprise flexible, partial cut-out sections to create an integrated hinge and perimeter reinforcement. Each tab 32 may be formed using a "U"-shaped cutout of the central body 36 to provide living hinge along one edge of the tab 32 so that the tab 32 is flexibly bendable relative to and independent of the central body 36. The integrated tabs 32 may fold outwards to permit the central body 36 of the padded restraint 30 to move somewhat with respect to the rigid support frame 22 while the tabs 32 are secured to the rigid support frame 22. This construction accommodates minor patient arm movements.

A rear portion (i.e., non-patient contact side) of the tabs further includes corresponding aggressive, releasable fasteners 34 compatible with the fasteners 28 utilized on the rigid support frame 22. The flexibility of the tabs 32 facilitates the usage of the padded restraint 30 to be wrapped and secured around the patient's arm. More specifically, the tabs 32 may be hinged in a manner that allows the permanent or re-closable fasteners 34 thereon to be connected directly to the mating fasteners 28 on the medial aspect of the vertical surface 26 of the rigid support frame 22. The tabs 32 are hinged in a manner that, when fastened to the rigid support frame 22, allows the central body 36 of the padded restraint 30 to be opened to encompass or contain the upper extremity. The tabs 32 may be adjusted to the left or right relative to the horizontal surface 24 of the rigid support frame 22 in order to provide desired or maximum coverage on the upper extremity. Still, it is contemplated that the fasteners could be permanently fastened to the rigid support frame 22.

Figure 4:
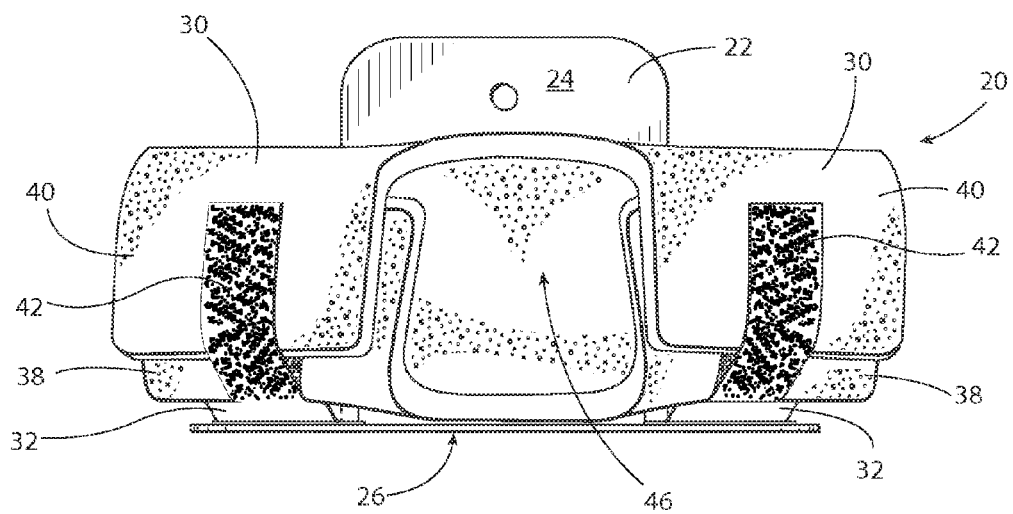
FIG. 4 illustrates a top view of the example padded restraint secured to the rigid support frame.

Once attached to the rigid support frame 22, and adjusted to the patient's upper extremity to maximize support and wrapped around the upper extremity, additional permanent or re-closable fasteners 42, 44 are employed to secure the position of said padded restraint 30 upon and encompassing the patient's upper extremity. As shown in the top view of FIG. 4, the additional fasteners 42, 44 may be secured to the padded restraint 30 in such a manner to allow a wrapping and closure about the patient's upper extremity. For example, each of the first pair of projections 38 of the padded restraint 30 can have one part of the re-closable fastener 42 secured thereto, while each of the second pair of projections 40 can have a corresponding second part of the re-closable fastener 44 secured thereto. The first part of the re-closable fastener 42 can be extend towards and/or be co-terminus with the edge of the first pair of projections 38, while the second part of the re-closable fastener 44 can extend a distance beyond the edge of the second pair of projections 40. Then, once the padded restraint 30 is wrapped into a cylindrical shape about the patient's arm, the second part of the re-closable fastener 44 can be pulled over to fasten onto the first part of the re-closable fastener 42 to secure the first and second pairs of projections 38, 40 together, as shown in FIG. 4. Preferably, the re-closable structure of the fasteners 42, 44 is fastenable along their length so that length of the closure is adjustable to thereby adjust the overall diameter of the cylindrical shape of the padded restraint 30 to be a custom fit upon the patient's arm.

Figure 5:
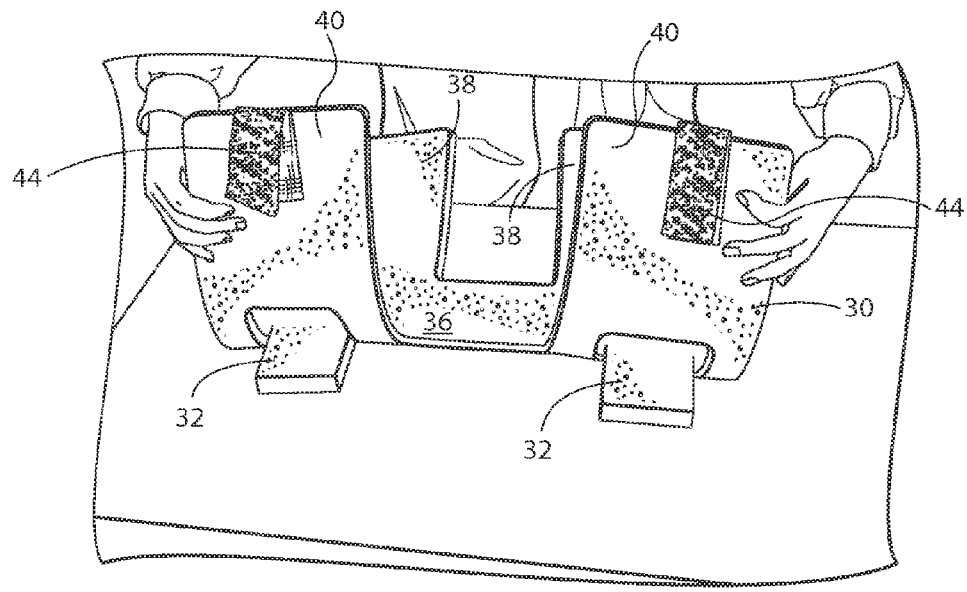
FIGS. 5-10 illustrate an example method of using the patent arm restraint system of the instant application.
Figure 6:
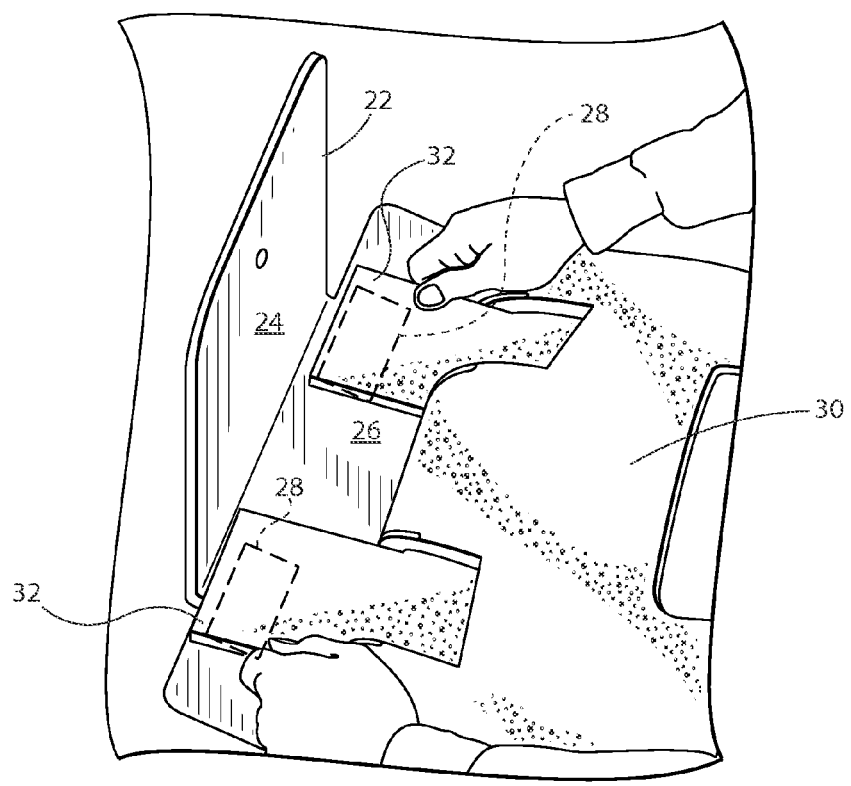

Turning to FIGS. 5-10, an example usage will be described. First the padded restraint 30 is placed face down upon a table or other surface, with the fasteners 34 of the tabs 32 exposed upwards. The tabs 32 are gently pulled upwards to separate them from the central body 36 of the padded restraint. Next, the padded restraint 30 is flipped over to be face up on the table or other surface. As shown in FIG. 5, the first and second pairs 38, 40 of projections are lifted upwards and generally towards each other so that the padded restraint 30 forms a "U"-shape, with the central body 36 remaining upon the table or surface. This geometry will separate the tabs 32 from the central body 36 and place them in a position to be secured to the rigid support frame 22. Turning to FIG. 6, the repositionable fasteners 34 of the tabs 32 are secured to the corresponding repositionable fasteners 28 on the medial aspect of the vertical surface 26 of the rigid support frame 22 and the padded restraint is held in place (horizontally and vertically). The user will locate the padded restraint 30 at the desired position upon the rigid support frame 22, and will secure the tabs 32 to the frame 22. At this stage, the padded restraint 30 is secured to and movable with the rigid support frame.

Figure 7:
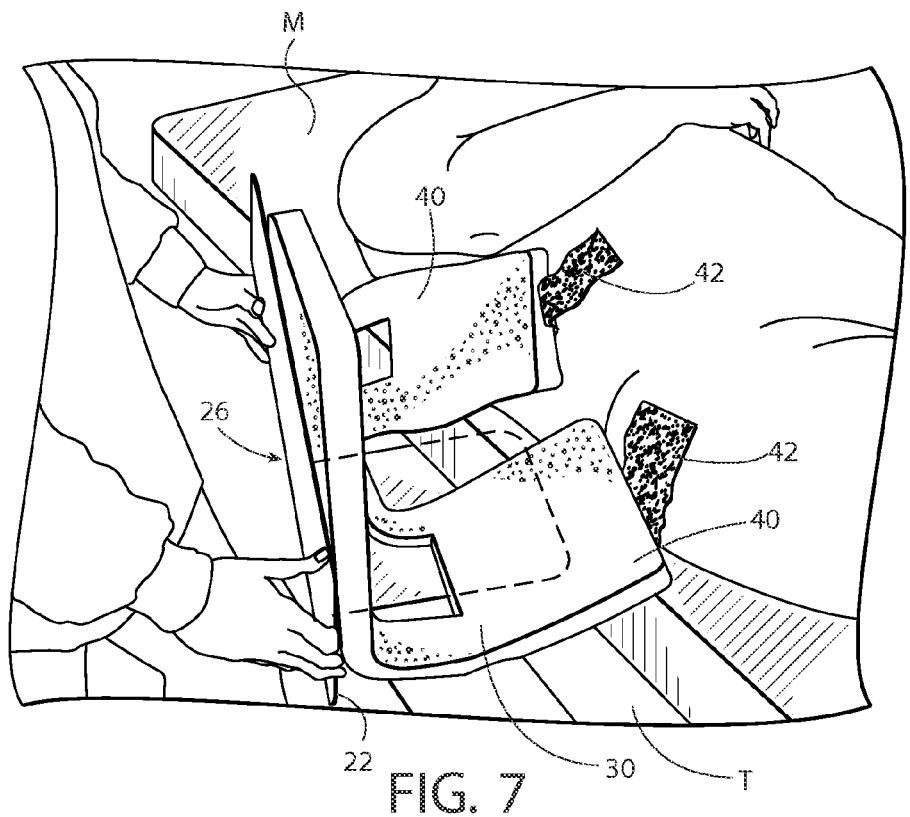
Figure 8:
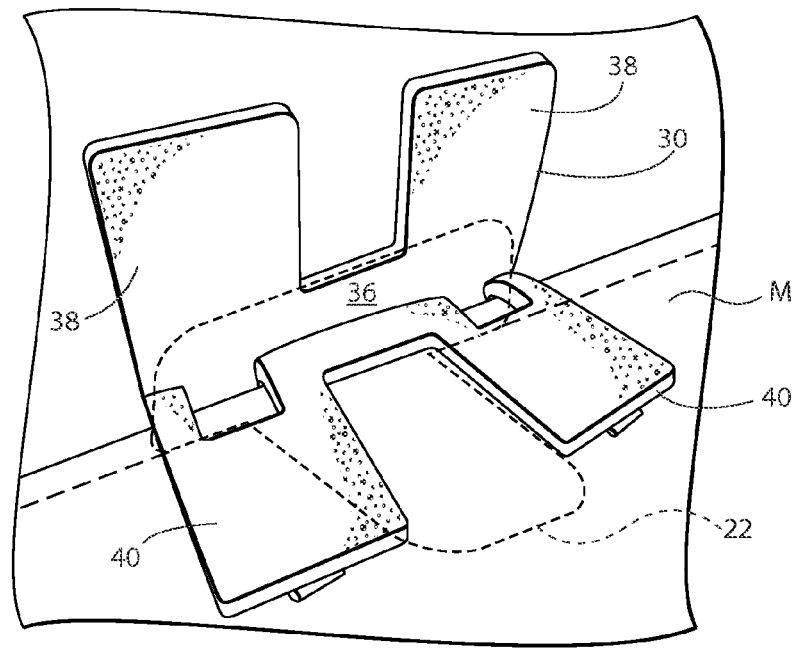

Next, as shown in FIG. 7, the rigid support frame 22 is placed in the desired operative position on the surgical table T and is coupled thereto. In the shown example, the horizontal surface 24 of the rigid support frame 22 is slid underneath the patient mattress M of the surgical table T to be held between the mattress M and the top surface of the surgical table T and held in place by friction and the weight of the lower torso of the patient. The familiar configuration will allow surgical assistants unobstructed access to the side of the operating room table or examination table. The position of the rigid support frame 22 and padded restraint 30, relative to the patient and surgical table T, may be adjusted at this time. As shown in FIG. 8, the rigid support frame 22 is pressed inwards towards the patient and surgical table T until it is snugly fit against the side of the mattress M. Alternatively, if the rigid support frame 22 is to be secured to the surgical table T via legs 29 or the like, these are secured at this time. Even so, the rigid support frame 22 will still appear as shown in FIG. 8. At this time, the tabs 32 are clamped between the vertical surface 26 of the rigid support frame 22 and the exterior side edge of the mattress M. The first and second pairs of projections 38, 40 form a generally "L"-shape and are ready to receive the patient's arm.

Figure 9:
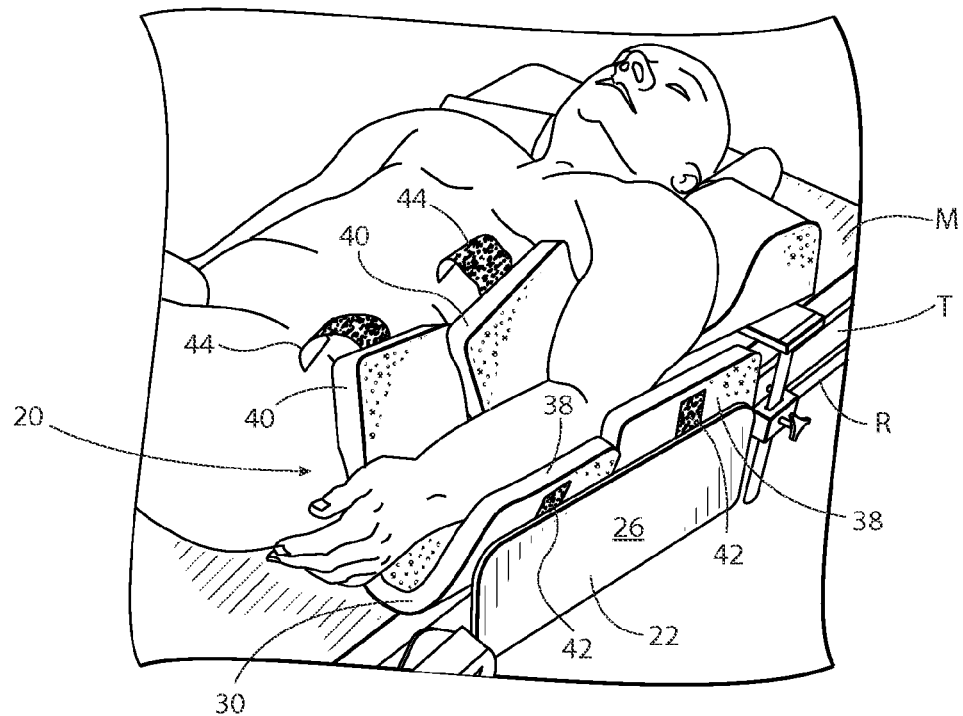
Figure 10:
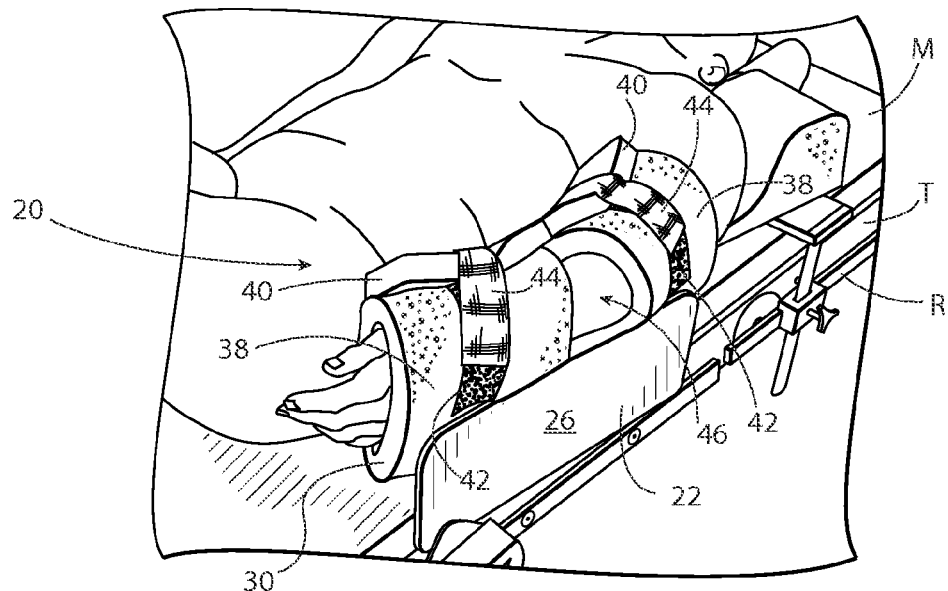

To secure the patient's arm within the padded restraint 30, as shown in FIG. 9, both the head facing and foot facing extension sections of the lateral portion of the arm strip (i.e., the outer portions of the "H"-shape) are each wrapped around the patient's arm. That is, both of the first and second pairs of projections 38, 40 are wrapped upwards to form a cylindrical geometry (e.g., see FIG. 4) to snugly retain the patient's arm. Preferably, portions of the first and second pairs of projections 38, 40 overlap each other. The medial section arm strips each have the repositionable fasteners 42, 44 (e.g., illustrated as hook-and-loop straps or belts) that are brought over the arm and attached to the corresponding fasteners 42, 44 on the lateral first and second pairs of projections 38, 40 of the corresponding side. Finally, as shown in FIG. 10, one end of a belt is attached to the medial side of the pad and the belt passes over the extremity and the distal end of the belt is attached to the opposite fastener. The belt is adjustable along its length and may be opened or closed many times to ensure a snug fit of the padded restraint 30 about the patient's arm. The padded restraint may also be adjusted on the rigid support frame 22 by repositioning the repositionable fastener tabs horizontally toward the patient's head or the feet. Desired coverage of the limb may be accomplished by adjusting the padded restraint to the desire position on the frame 22. This allows protection of fingers and nerves and serves to minimize compression. Additionally, the recloseable fasteners permit the anesthesia team easy and immediate access to IV lines and monitoring lines by partially or completely opening up the padded restraint. Additionally, when the first and second pairs of projections 38, 40 are wrapped upwards to form a cylindrical geometry, an at least partial alignment of first and second cutouts 39, 41 provides an upward access opening 46 extending through the padded restraint to the patient's arm in the normal operational position (see FIG. 4). Even in the regular course of a surgical procedure, this upward access opening 46 provides medical personnel with fast and easy anesthesia access and exposure to the patient's arm, as well as IV lines, monitoring lines and ports. As can be appreciated, greater alignment of the first and second cutouts 39, 41 can provide a relatively larger upward access opening 46. In addition or alternatively, different alignments of the first and second cutouts 39, 41 and/or specific geometry of the first and second cutouts 39, 41 (or even additional cutouts) could be used to provide specialized access openings for particular desired purposes and/or at particular locations or orientations. Finally, once both of the repositionable fasteners 42, 44 on the first and second pairs of projections 38, 40 are coupled together, the patient's arm is secured to the surgical table T. The process is repeated for each arm.

It is typical that padded restraints may be advantageously employed in medical procedures requiring the supine position including flat, lateral tilt or head down supine position (Trendelenburg) and is used bilaterally to support both limbs. In some embodiments, a device combines the use of several restraint, support or stabilizing devices embodied in the claims to restrain the patient's arm. For example, two padded restraints mounted on sleds may be used to restrain and position a patient's arms for those gynecological, cystoscopic and urological lithotomy procedures.

Figure 11:
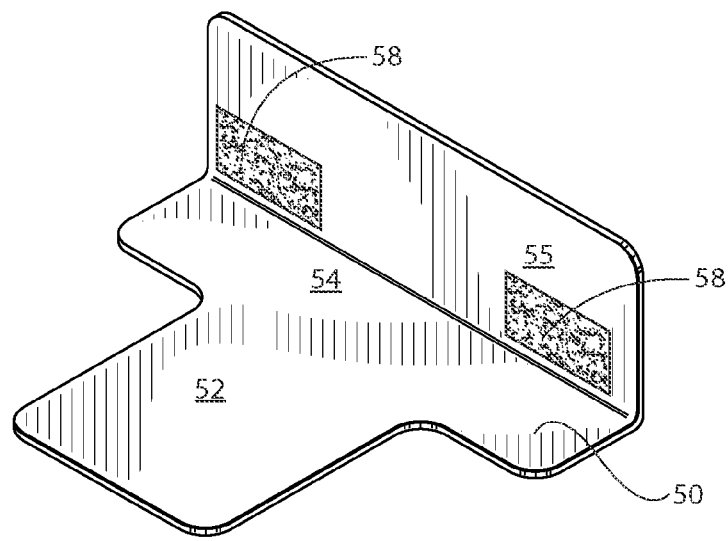
FIG. 11 illustrates a perspective view of a second example rigid support frame.
Figure 12:
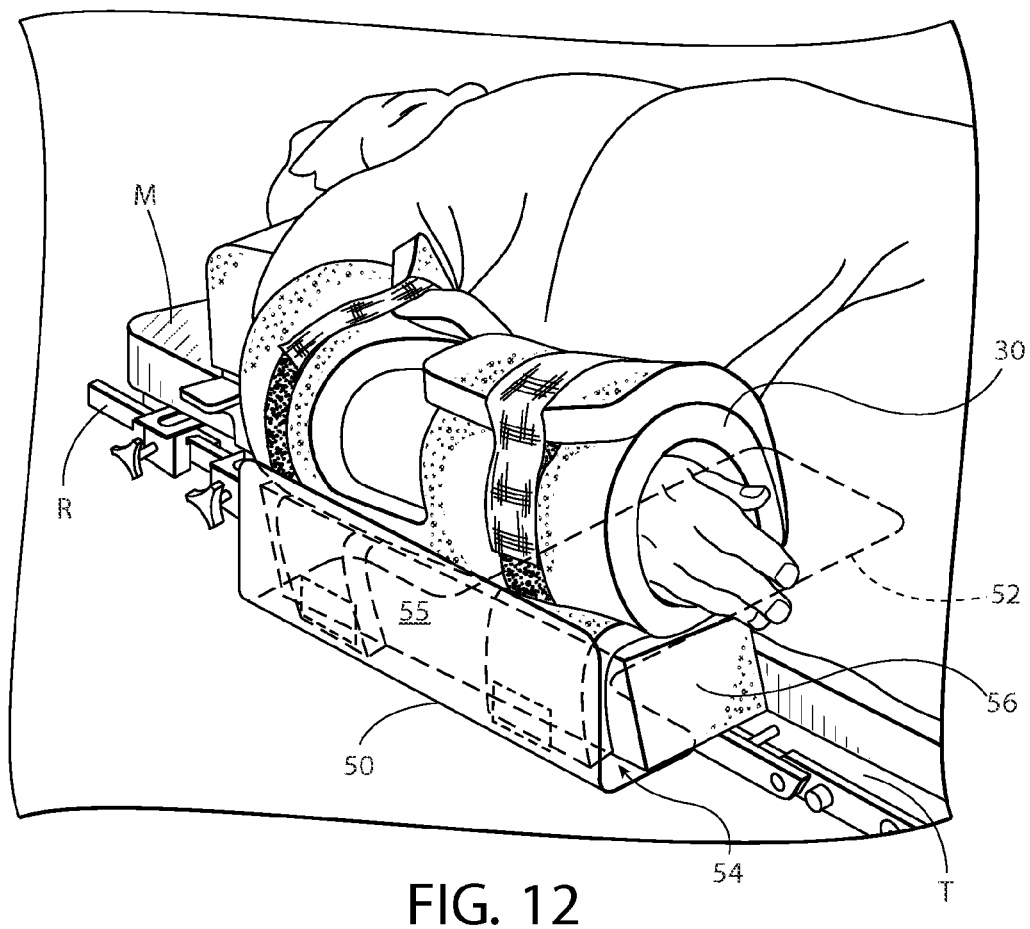
FIG. 12 illustrates an example usage of the second example rigid support frame.

Turning now to FIGS. 11-12, the arm restraint system, in addition or alternatively, can include a width extender to easily accommodate the arms of patients with a high body-mass index (BMI). For example, a second example rigid support frame 50 can have an increased width in the horizontal direction, and may also have an increased height in the vertical direction. In the shown example, the horizontal surface 52 can include an auxiliary horizontal surface 54 that can thereby increase the width of the rigid support frame 50. Preferably, the auxiliary horizontal surface 54 extends along the entire lateral edge of the rigid support frame 50, such as substantially coextensive with the vertical surface 55 (although the auxiliary surface 54 can be wider or shorter). The main horizontal surface 52 (which extends underneath the table mattress M) may have a relatively narrower profile to avoid contact with other parts of the surgical table T top. The vertical surface 55 can incorporate an aggressive releasable fastening system 58 of the types previously described herein (i.e., fastening system 28). A bariatric extender pad 56 or block may be used between the rigid support frame 50 and the padded restraint 30 to properly position the patient's larger arm. In one example, the extended bariatric version can add 4 inches of width and can keep the patient's arms at the same level as the table pad to safely secure the arms of patients up to 750 lbs. That is, the auxiliary horizontal surface 54 can add the desired extra 4 inches to effectively re-locate the vertical surface of the rigid support frame 50 laterally outward of the surgical table T. The bariatric extender pad 56 or block can have various shapes and sizes, such as 2" tall×3" wide×20" long, although other sizes are contemplated. Preferably, the bariatric extender pad 56 or block has an installed height generally similar to the height of the surgical table T mattress M. Preferably, the bariatric extender pad 56 or block is made of the same or similar deformable material as the padded restraint. The bariatric extender pad 56 or block can be permanently or removably secured to either of the sled or padded restraint, such as held in place by friction due to the weight of the patient's arm, or secured to the rigid support frame 50 by re-positionable fasteners similar to those described herein, or even secured by permanent fasteners. In use, it is contemplated that the bariatric extender pad 56 or block is coupled to the rigid support frame 50 after the padded restraint 30, but prior to securing the rigid support frame 50 to the surgical table T. The padded restraint 30 can be substantially similar to that previously described herein, which may be attached to the second example rigid support frame 50 in substantially the same manner.

The invention creates an environment for patient safety that is capable of maintaining the arms of patients with normal and high body mass indexes restrained in a familiar position at the side of the body while maintaining the arm at mattress M level. It eliminates the need for a draw sheet that when used to create a tucking restraint for the arm creates undue compression on nerves. The H shape of the pad (providing the upward access opening 46) and the recloseable fasteners permit the anesthesia team easy and immediate access to IV and monitoring lines regardless of the inclination of the surgical table T and the recloseable fasteners permit a fast, safe and secure method to re-secure the arm. The low profile of the frame secures the patient restraint pad to assure arm security, and the low profile does not clash with the robot arm. Moreover, the physical profile of the device is not bothersome to surgical assistants.

The invention successfully reduces the risk for operating room acquired patient arm injuries while providing a stable horizontal, vertical and lateral restraint platform for the upper extremities during the patient's experience on the operating room table. I have discovered that creating a fully adjustable arm restraint that utilizes the ergonomic advantages of a modified "toboggan" and the safety and stability of an arm restraint system that does not come from under the body can provide improved access for anesthesia to the arm, eliminate clash between robotic arms and the arm stabilizer, reduce anesthesia time and improve patient outcomes. Some of the innovative elements of the invention include, without limitation, the combination of a multiply adjustable H shaped arm restraint with built in stabilizing tabs and the low profile arm coupler.

No other design has attempted to solve these issues in this manner. There are few inventors working on patient positioning products for the operating room and the concept of creating a hybrid utilizing the features of two dissimilar technologies has not been apparent to others. My unique clinical experience, design background, and intimacy in the marketplace are the reason that I am the only person who has created such a device.

The following definitions are provided for terms used herein.

Supine: The patient lays on the table on their back.

Trendelenburg: The table is tilted in the head down position (typically 1 degree to 60 degrees).

Toboggan: Arm restraint that encompasses the arm—named after appearance.

Sled: Arm restraint that holds the restraint pad that encompasses the arm—named after appearance.

Draw Sheet: woven or non-woven sheet placed transversely across the operating room table. Typically used to assist in moving patients. The excess on each side is conventionally used to tuck patient arms.

Neuropathy: An injury to a nerve.

Easily re-closable fasteners: Common reference to hook and loop fasteners (one commercial example is VEL-CRO®).

Anesthesia monitoring lines: Electrically conductive lines attaching certain parts of the body to monitoring systems.

Robot arm: An appendage of the surgical robot (such as the Da Vinci robot) that is capable of holding and operating certain surgical instruments.

AORN: An association of operating room nurses. Considered the governing body with regards to certain guidelines including patient positioning.

IV Infiltration: Typical result of the displacement of the IV needle from the vein into adjoining tissues causing swelling or edema.

Compartment Syndrome: Damage of muscle that is encapsulated in fascia resulting in internal pressures capable of disrupting blood flow to the structure.

Ergonomic arm's length: Anthropomorphic images—showing surgeon stance with arms lowered and 90 degrees to patient.

Surgical Drape: A sterile covering material that typically utilizes a fenestration to isolate the surgical site from the patient. Typical drapes will cover an area approximately 50% larger than the patient.

Lateral: away from the midline.

Medial: toward the midline.

Egg crate foam: Typical a low density foam. Named based on the appearance of the foam configuration.

Surgical table T accessory rail: Most surgical table Ts have an accessory rail on each side that runs parallel with the table top. They are typically segmented to allow free articulation of table sections.

BMI ratings: A formula utilizing patient size and weight has been utilized to determine.

Body Mass Index: The higher the BMI the more obese the patient.

Perineal cutout: This feature on operating room tables permits optimal access to the patient's perineum.

Perineum: The area located between reproductive structures and the anus.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. An arm restraint system for restraining movement of an arm of a patient's body lying over a top surface of a table, comprising: a rigid support frame located at a lateral edge of said table adjacent to the arm of said patient's body, and the rigid support frame comprising a horizontal surface capable of being positioned between said table and a mattress lying over a top surface of said table and a vertical surface extending upwards from the horizontal surface and comprising a first repositionable fastener thereon; and a padded restraint configured to be disposed over a top surface of the mattress, and the padded restrain configured to at least partially receive the arm of said patient and including a deformable material, the padded restraint comprising:
   a central body,
   a pair of cutouts formed in the central body and surrounded by a surface of the central body, each cutout defining at least two sides of a corresponding tab, each tab having an additional side connected to the central body to define a living hinge of the tab, the pair of tabs being independently movable relative to each other and the central body between a first position wherein the tabs are received in an opening bounded by the cutouts and a second position wherein the tabs protrude from the surface of the central body, the tabs further comprising a second repositionable fastener that is compatible with the first repositionable fastener,
   wherein each tab is monolithic with the central body, a pair of first projections monolithic with the central body, the pair of first projections extending outwards from the central body and comprising a third repositionable fastener thereon, and a pair of second projections monolithic with the central body, the pair of second projections located opposite the pair of first projections and extending outwards from the central body and comprising a fourth repositionable fastener thereon that is compatible with the third repositionable fastener, wherein the padded restraint can be wrapped in a tubular geometry about the patient's arm, with the first pair of projections and the second pair of projections in an overlying arrangement, and secured upon the patient's arm via engagement of the third and fourth repositionable fasteners, and wherein the padded restraint is securely fixed to the vertical surface of the rigid support frame, via engagement of the second repositionable fastener of the pair of tabs and the first repositionable fastener of the rigid support frame, to inhibit movement of the patient's arm relative to the rigid support frame and thereby maintain the arm at a position laterally adjacent to the patient's body without the arm being restrained by tucking.

2. The arm restraint system of claim 1, wherein the padded restraint is made of a polyether-type polyurethane foam and has a density of at least 1 lbs per cubic foot.

3. The arm restraint system of claim 1, wherein the first and second repositionable fasteners each comprises a hook-and-loop type fastener.

4. The arm restraint system of claim 1, wherein the first repositionable fastener comprises at least two separate fasteners disposed at separate locations upon the vertical surface of the rigid support frame, wherein the separate locations of the at least two separate fasteners are spaced apart a distance corresponding to a separation distance between the pair of tabs of the padded restraint.

5. The arm restraint system of claim 1, wherein the first repositionable fastener comprises at a single fastener extending across a substantial width of the vertical surface.

6. The arm restraint system of claim 1, wherein the horizontal surface of the rigid support frame is substantially perpendicular to the vertical surface.

7. The arm restraint system of claim 1, wherein the horizontal surface comprises at least one hole extending therethrough.

8. The arm restraint system of claim 1, wherein the rigid support frame further comprises an auxiliary horizontal surface that increases a width of the rigid support frame along a horizontal direction substantially parallel to said top surface of said table.

9. The arm restraint system of claim 8, wherein the arm restraint system further comprises a bariatric extender pad supported upon the auxiliary horizontal surface to be thereby disposed between the rigid support frame and the padded restraint.

10. The arm restraint system of claim 1, wherein the third and fourth repositionable fasteners are hook-and-loop type fasteners, and one of the third or fourth repositionable fasteners is provided upon a strap that extends a distance beyond an edge of the padded restraint.

11. The arm restraint system of claim 1, wherein each tab is centrally located generally between the first pair of projections and the second pair of projections.

12. The arm restraint system of claim 1, wherein the cutouts are "U"-shaped and the living hinge of the corresponding tab is disposed between legs of the "U"-shaped cutout.

13. The arm restraint system of claim 1, wherein substantially all of a rear non-patient contact side of each tab comprises the second repositionable fastener.

14. The arm restraint system of claim 1, wherein the rigid support frame is hard mounted to a rail of the table.

15. The arm restraint system of claim 1, wherein the rigid support frame is positionably adjustable relative to a rail of the table.

* * * * *